(12) United States Patent
Shimomura et al.

(10) Patent No.: US 10,856,732 B2
(45) Date of Patent: Dec. 8, 2020

(54) ENDOSCOPE SYSTEM WITH PROCESSOR SIDE CONNECTOR

(71) Applicant: FUJIFILM Corporation, Tokyo (JP)

(72) Inventors: Koji Shimomura, Kanagawa (JP); Satoshi Narita, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 828 days.

(21) Appl. No.: 15/379,500

(22) Filed: Dec. 15, 2016

(65) Prior Publication Data

US 2017/0172400 A1 Jun. 22, 2017

(30) Foreign Application Priority Data

Dec. 17, 2015 (JP) .................. 2015-245970

(51) Int. Cl.
*A61B 1/12* (2006.01)
*A61B 1/00* (2006.01)

(52) U.S. Cl.
CPC .......... *A61B 1/126* (2013.01); *A61B 1/00013* (2013.01); *A61B 1/00105* (2013.01); *A61B 1/00126* (2013.01); *A61B 1/00128* (2013.01); *A61B 1/128* (2013.01)

(58) Field of Classification Search
CPC . A61B 1/126; A61B 1/00013; A61B 1/00105; A61B 1/00126; A61B 1/00128; A61B 1/128
See application file for complete search history.

(56) References Cited

U.S. PATENT DOCUMENTS

| 6,099,465 A | 8/2000 | Inoue |
| 2002/0022829 A1* | 2/2002 | Nagase .................. A61B 18/20 606/12 |

(Continued)

FOREIGN PATENT DOCUMENTS

| JP | H06133919 | 5/1994 |
| JP | H06251829 | 9/1994 |

(Continued)

OTHER PUBLICATIONS

Office Action of Japan Counterpart Application, with English translation thereof, dated Oct. 24, 2018, pp. 1-11.

(Continued)

*Primary Examiner* — Timothy J Neal
*Assistant Examiner* — William B Chou
(74) *Attorney, Agent, or Firm* — JCIPRNET

(57) ABSTRACT

An endoscope system includes an endoscope having an image pickup section and a processor device for an endoscope, and optically communicates signals through a scope-side connector and a processor-side connector. In the endoscope system, an optical communication section is constituted by an image signal transmission section and an image signal reception section, and windows and are arranged. An optical communication section is constituted by a scope-side signal transception section and a processor-side signal transception section, and windows and are arranged. The endoscope system includes: a first air blowing section and a second air blowing section for removing dirt adhered on the windows; and a control section that controls the first air blowing section and the second air blowing section.

9 Claims, 12 Drawing Sheets

(56) References Cited

U.S. PATENT DOCUMENTS

| | | | | |
|---|---|---|---|---|
| 2014/0128886 A1* | 5/2014 | Holop | ............... | A61B 18/14 |
| | | | | 606/130 |
| 2016/0073855 A1* | 3/2016 | Farr | ............... | A61B 1/00154 |
| | | | | 600/109 |
| 2016/0150944 A1* | 6/2016 | Tearney | ............ | A61B 1/00177 |
| | | | | 600/109 |
| 2017/0049301 A1* | 2/2017 | Hagihara | ........... | A61B 1/00006 |
| 2020/0187752 A1* | 6/2020 | Williams | ........... | A61B 1/00016 |

FOREIGN PATENT DOCUMENTS

| | | | |
|---|---|---|---|
| JP | H10155740 | | 6/1998 |
| JP | 2008148935 | | 7/2008 |
| JP | 2010088657 | | 4/2010 |
| JP | 2010088657 A | * | 4/2010 |
| JP | 2013-192796 | | 9/2013 |
| JP | 2015160098 | | 9/2015 |

OTHER PUBLICATIONS

"Office Action of China Counterpart Application," with English translation thereof, dated Jan. 6, 2020, p. 1-p. 19.
"Office Action of China Counterpart Application" with English translation thereof, dated Aug. 3, 2020, pp. 1-17.

\* cited by examiner

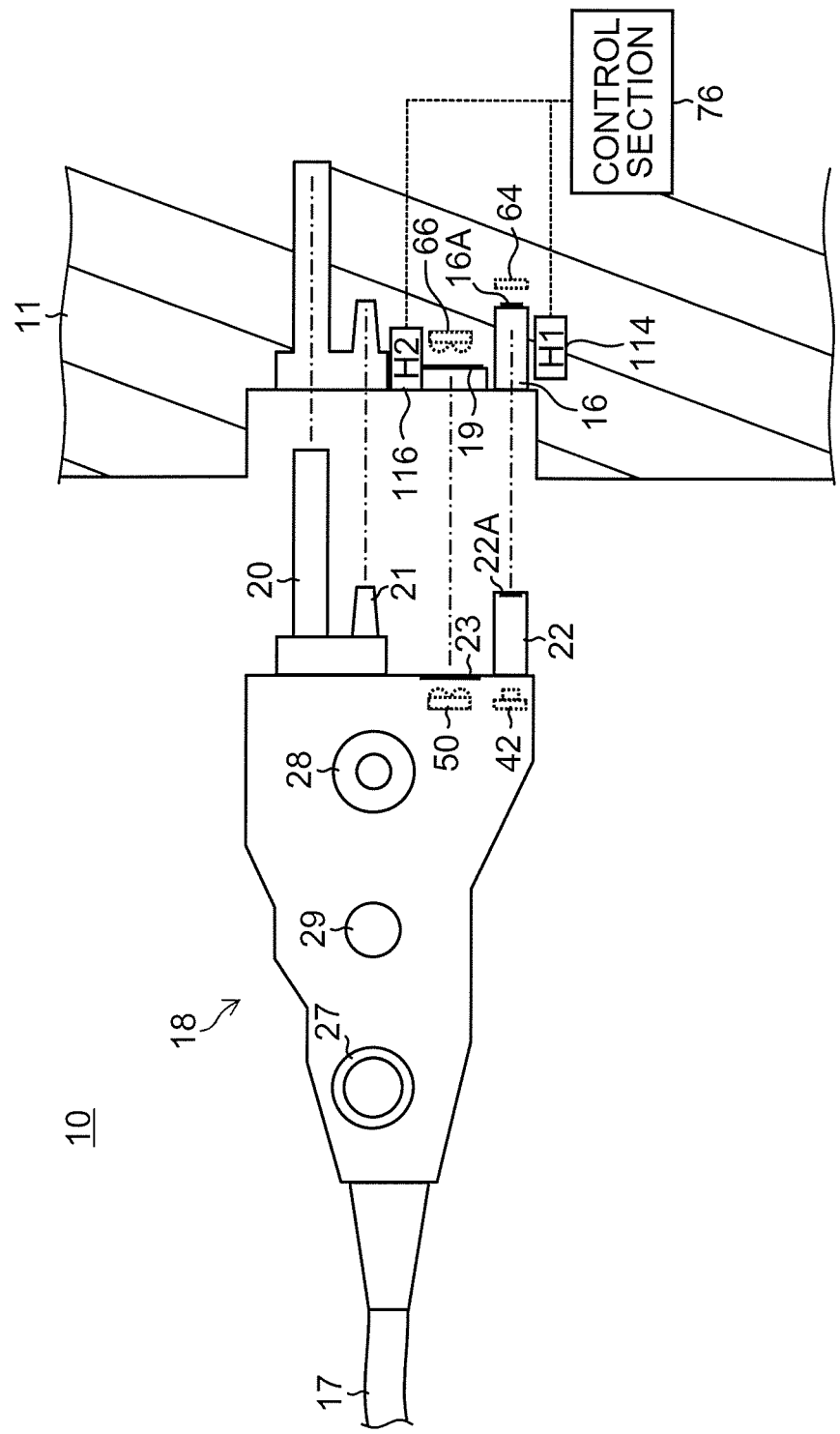

ENDOSCOPE SYSTEM WITH PROCESSOR SIDE CONNECTOR

CROSS-REFERENCE TO RELATED APPLICATIONS

The present application claims priority under 35 U.S.C. § 119 to Japanese Patent Application No. 2015-245970, filed on Dec. 17, 2015. The above application is hereby expressly incorporated by reference, in its entirety, into the present application.

BACKGROUND OF THE INVENTION

Field of the Invention

The present invention relates to an endoscope system, and relates to an endoscope system that optically communicates signals between an endoscope and a processor device for the endoscope, by a non-contact method.

Description of the Related Art

Generally, an endoscope system is composed of: endoscope including an image pickup section such as a CCD (Charge Coupled Device) image sensor that images the inside of a body cavity, and a connector portion that is provided in an end of a universal cord; and a processor device for the endoscope including a connector portion at which the connector portion of the endoscope is removably fit, a control section that subjects image signals output from the endoscope to image processing and the like, and a light source.

In the endoscope system, the connector portion of the endoscope and the connector portion of the processor device for the endoscope are connected by an electric contact, thereby an electric power is supplied from the processor device for the endoscope to the endoscope, and image signals and control signals are transmitted between the processor device for the endoscope and the endoscope.

In the endoscope system, it is necessary to clean and disinfect the endoscope after use. Because of this, it is necessary to attach a waterproof cap that protects the electric contact, to the connector portion of the endoscope. However, it takes time and effort to attach and detach the waterproof cap, and besides there has been a problem that the electric contact is damaged when it has been forgotten to attach the waterproof cap.

In order to cope with such a problem, an endoscope system described in Japanese Patent Application Laid-Open No. H10-155740 is configured to provide an optical communication section for optically communicating the image signals and the control signals between the endoscope and the processor device for the endoscope, and provide a power supply section that supplies an electric power from the processor device for the endoscope to the endoscope by a non-contact method.

In addition, an endoscope system described in Japanese Patent Application Laid-Open No. 2013-192796 includes: a transmission section which converts the image signal of the endoscope into a light signal, and transmits the light signal to the processor device for the endoscope; and a control section that controls the transmission output characteristics of the light signal.

SUMMARY OF THE INVENTION

By the way, in the case where signals such as image signals and control signals are optically communicated between a processor device for the endoscope and the endoscope, if dirt such as a water droplet, fogging and dust presents on an optical member that is arranged in an optical path, appropriate optical communication cannot be performed.

The present invention is designed with respect to such a circumstance, and aims to provide an endoscope system that can adequately perform optical communication of the signals between the processor device for the endoscope and the endoscope.

According to one aspect of the present invention, An endoscope system which includes an endoscope having an image pickup section and a processor device for an endoscope, and optically communicates signals through a scope-side connector of the endoscope and a processor-side connector of the processor device for the endoscope, comprising: an optical communication section configured to optically communicate signals; an optical member that is arranged in an optical path of the optical communication section; a removing section configured to remove dirt adhered on the optical member; and a control section configured to control an operation of the removing section.

It is preferable that the removing section is an air blowing section configured to blow gas toward the optical member.

It is preferable that the processor device for the endoscope comprises a gas feeding section configured to supply a pressurized gas to the endoscope, and the gas is fed from the gas feeding section to the air blowing section.

It is preferable that the removing section is a wiper section configured to wipe the optical member.

It is preferable that the removing section is a heating section configured to heat the optical member.

It is preferable that the control section detects whether or not the scope-side connector and the processor-side connector are connected to each other, and controls the removing section.

It is preferable that the control section controls the removing section based on an input value of the optical communication section.

It is preferable that the control section controls an output value based on the input value of the optical communication section.

It is preferable that the control section controls the removing section in response to an operation of a manual switch.

According to another aspect of the present invention, an endoscope system which includes an endoscope having an image pickup section and a processor device for an endoscope, and optically communicates image signals and control signals through a scope-side connector of the endoscope and a processor-side connector of the processor device for the endoscope, comprising: an image signal transmission section which is provided in the scope-side connector and is configured to transmit the image signal of the image pickup section as an optical signal; a scope-side signal transception section which is provided in the scope-side connector and is configured to optically communicate the control signal; an image signal reception section which is provided in the processor-side connector and is configured to receive the optical signal from the image signal transmission section of the endoscope; a processor-side signal transception section which is provided in the processor-side connector and is configured to optically communicate with the scope-side signal transception section; a removing section configured to remove dirt adhered on an optical member for an image signal which is arranged in an optical path between the image signal transmission section and the image signal reception section, and/or an optical member for a control signal which is arranged in an optical path between the scope-side signal transception section and the processor-side signal transception section; and a control section that controls an operation of the removing section.

It is preferable that the scope-side connector comprises a power receiving section that includes a power receiving coil configured to receive an electric power from the processor device for the endoscope in a non-contact manner, and the processor-side connector comprises a power feeding section that includes a power feeding coil configured to feed the electric power to the endoscope in a non-contact manner.

The endoscope system according to the present invention can adequately perform optical communication of signals between the processor device for the endoscope and the endoscope.

BRIEF DESCRIPTION OF THE DRAWINGS

FIG. 14 is a sectional view that enlarges the scope-side connector and the processor-side connector according to the third embodiment.

DETAILED DESCRIPTION OF THE EMBODIMENTS

Figure 1:
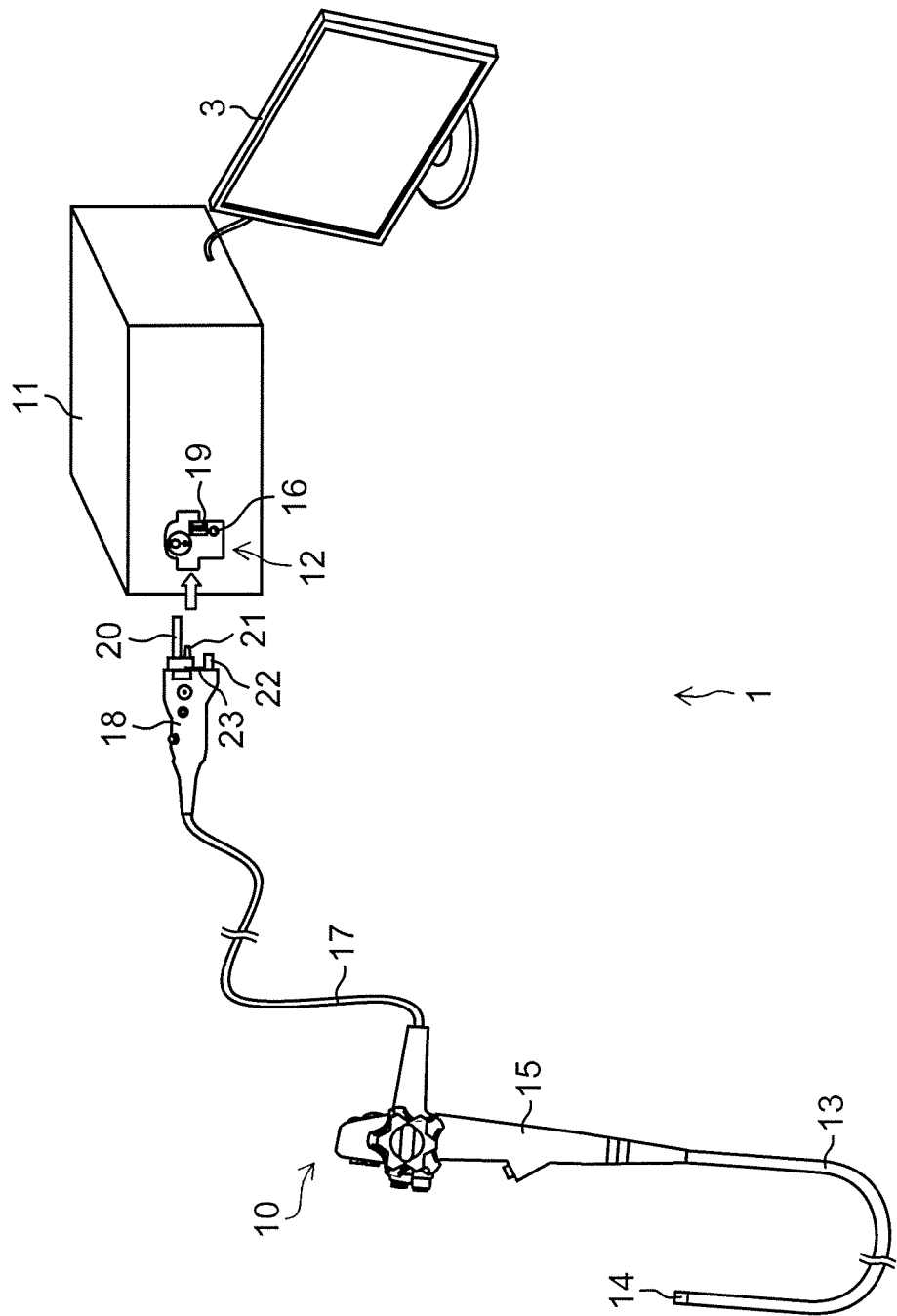
FIG. 1 is an outside drawing that shows an endoscope system.

Preferable embodiments according to the present invention are described below with reference to the attached drawings. The present invention is described with reference to the following preferable embodiments. The present invention can be modified by many techniques without exceeding the scope of the present invention, and can make use of other embodiments than the present embodiment. Accordingly, all modifications in the range of the present invention are included in the claims.

Here, in the figure, portions designated by the same reference characters are similar elements having similar functions. In addition, in the present specification, when a range of numeric values is expressed by "to", the numerical values of the lower limit and the upper limit expressed by "to" shall be also included in the range of the numeric values.

Preferable embodiments of the endoscope system according to the present invention are described below with reference to the attached drawings.

[Endoscope System]

FIG. 1 is an outside drawing that shows an endoscope system according to the present invention.

As is shown in FIG. 1, an endoscope system 1 includes an endoscope 10 and a processor device 11 for an endoscope.

The endoscope 10 illustrates a flexible scope. The endoscope 10 includes: a flexible insertion section 13 that is to be inserted into a body cavity of a patient; an operation section 15 which is arranged in a proximal end portion of the insertion section 13; a universal cord 17 which is arranged in the operation section 15; and a scope-side connector 18 which is provided on an end of the universal cord 17. The scope-side connector 18 is connected to a processor-side connector 12 that functions as a mounting part of the processor device 11 for the endoscope.

As is described later, the endoscope system 1 of the present embodiment transmits an electric power, image signals and control signals by a non-contact method between the endoscope 10 and the processor device 11 for the endoscope, through a connector section that is formed of the scope-side connector 18 and the processor-side connector 12. The endoscope 10 is not limited to the flexible scope, and may be another type of endoscope such as a rigid scope.

An observation window, an illumination window and the like are provided on a distal end face of the insertion section 13. On a distal end portion 14 that constitutes the distal end of the insertion section 13, there are arranged: an objective optical system which images an object light that has been emitted from an observation site and is taken in through an observation window, as an optical image; an image pickup section that converts the optical image that has been formed by the objective optical system into an electric signal; and the like.

The image signal that is output from the image pickup section is transmitted to an image signal transmission section 42 (FIG. 2), by a transmission cable that has been inserted and arranged up to the scope-side connector 18 through the inside of the insertion section 13, the operation section 15 and the universal cord 17. The image signal is converted into an optical signal by the image signal transmission section 42 that is arranged on the scope-side connector 18, and is optically transmitted to an image signal reception section 64 (FIG. 2) that is arranged in the processor-side connector 12 of the processor device 11 for the endoscope, in a non-contact manner.

A shaft 22 which projects toward the processor device 11 for the endoscope is provided on the scope-side connector 18. On the other hand, a hole 16 into which the shaft 22 is to be inserted is provided in the processor-side connector 12. The shaft 22 is inserted into the hole 16, which thereby aligns the image signal transmission section 42 with the image signal reception section 64.

On the distal end portion 14, a light-emitting section of a light guide 52 (FIG. 2) is arranged that transmits a light for illuminating the observation site, through the illumination window. The light guide 52 is inserted and arranged up to the scope-side connector 18 through the inside of the insertion section 13, the operation section 15 and the universal cord 17. A light guide rod 20 that is connected to the light guide 52 projects from the scope-side connector 18.

In the operation section 15, there are provided: an angle knob for adjusting the direction of the distal end face of the insertion section 13 in vertical and horizontal directions; an air/water feed button for spouting air or water from the distal end face of the insertion section 13; a release button for recording the endoscope image as a still picture; and the like. The direction of the distal end face of the insertion section 13 is adjusted by bending a bending portion that is provided in the vicinity of the proximal end side of the distal end portion 14.

The universal cord 17 is covered with an outer wall portion that is thin and long tubular, and has flexibility. In a cavity in the inside of the outer wall portion, there are inserted and arranged: a transmission cable that is inserted and arranged in the cavity portion in the inside of the insertion section 13 and the inside of the operation section 15; the light guide 52; the air/water feed tube; and the like.

On the scope-side connector 18, an air feed fitting 21 is provided which projects in the same direction as the light guide rod 20.

In the scope-side connector 18 of the endoscope 10, there is provided a scope-side signal transception section (scope-side signal transmission and reception section) 50 (FIG. 2) that optically transmits and receives control signals which controls the image pickup section, power-receiving information which is used in control of non-contact power feeding, and the like, in a non-contact manner. In the processor-side connector 12 of the processor device 11 for the endoscope, there is a processor-side signal transception section (processor-side signal transmission and reception section) 66 (FIG. 2) that optically transmits and receives the signals with the scope-side signal transception section 50 of the endoscope 10, in a non-contact manner.

The optical communication is performed between the scope-side signal transception section 50 and the processor-side signal transception section 66, through windows 19 and 23 which are optical members.

In addition, a monitor 3 that is a display device is connected to the processor device 11 for the endoscope. The monitor 3 displays an image of the observation site, and the like.

Figure 2:
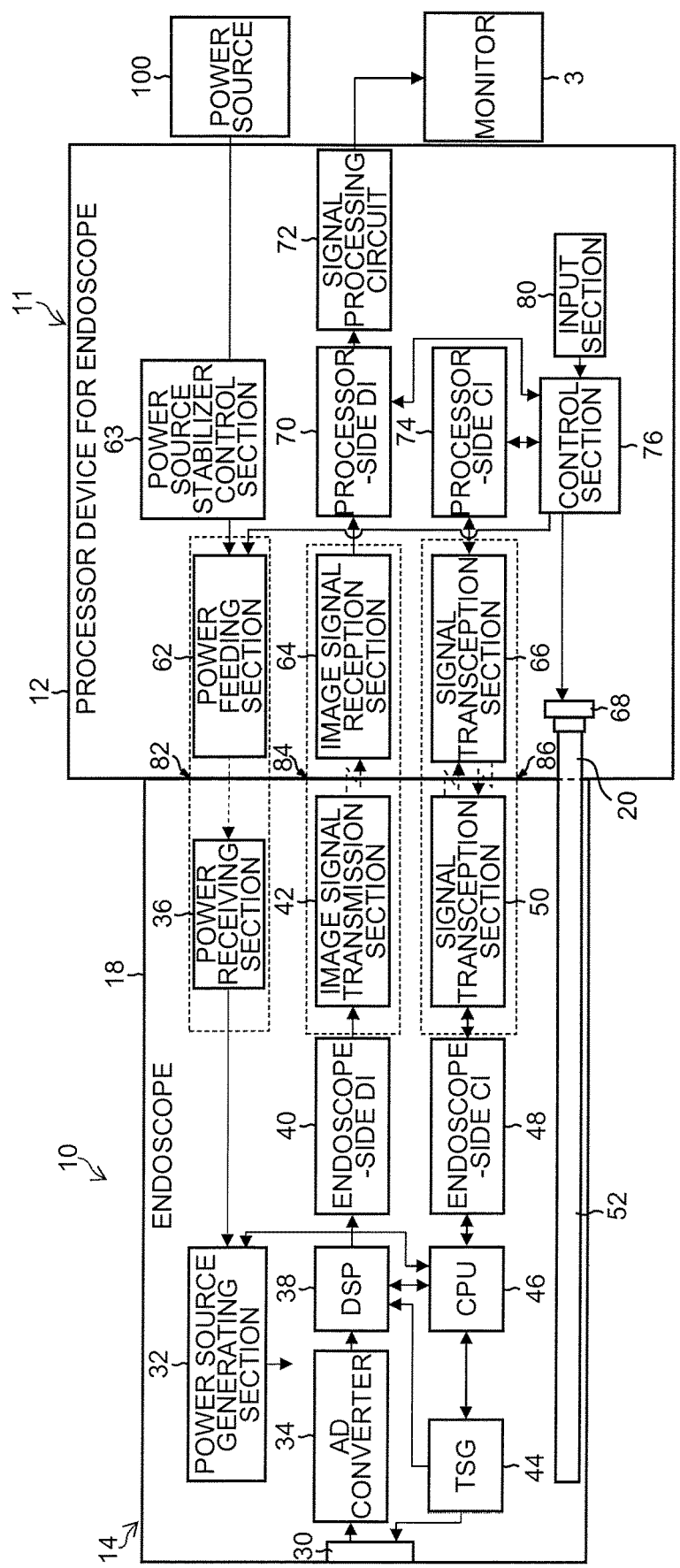
FIG. 2 is a block diagram showing an internal structure of the endoscope system.

FIG. 2 is a block diagram showing an internal structure of the endoscope system 1 of FIG. 1.

When the endoscope 10 is used, the scope-side connector 18 of the endoscope 10 is connected to the processor-side connector 12 of the processor device 11 for the endoscope. When the scope-side connector 18 is connected to the processor-side connector 12, the power supply and reception, optical communication of image signals, and optical communication of various control signals are performed between the scope-side connector 18 and the processor-side connector 12 by a non-contact method.

In the scope-side connector 18 of the endoscope 10, there are provided: a power receiving section 36 that receives an electric power by a non-contact method; an image signal transmission section 42 that optically transmits image signals of the image pickup section 30 by a non-contact method; and a scope-side signal transception section 50 that optically transmits and receives control signals which control the image pickup section 30, the power receiving information which is used for the control of non-contact power feeding, and the like, by a non-contact method.

The scope-side connector 18 of the endoscope 10 is connected to the processor-side connector 12 of the processor device 11 for the endoscope. The processor device 11 for the endoscope supplies (feeds electric power) an electric power to the endoscope 10 that is connected (attached) to the processor-side connector 12, and transmits and receives various signals to and from the endoscope 10.

The processor device 11 for the endoscope is provided with a light source 68. The illumination light emitted from the light source 68 is supplied to the light guide 52 through the light guide rod 20, and the light is transmitted to the distal end portion 14 through the light guide 52.

In the processor-side connector 12 of the processor device 11 for the endoscope, which is connected to the scope-side connector 18 of the endoscope 10, there are provided: a power feeding section 62 that feeds an electric power to the power receiving section 36 of the endoscope 10 in a non-contact manner; an image signal reception section 64 that receives the image signal sent from the image signal transmission section 42 of the endoscope 10 in a non-contact manner; and a processor-side signal transception section 66 that transmits and receives the signal to and from the scope-side signal transception section 50 of the endoscope 10, in a non-contact manner.

The processor device 11 for the endoscope takes in the image signal that has been output from the image pickup section 30 of the distal end portion 14 of the endoscope 10, subjects the taken-in image signal to various signal processes, and generates image data that constructs a video (moving image) or a still image of the observation site. The generated image data is output to the monitor 3 that is connected to the processor device 11 by a cable, and the image of the observation site and the like are displayed on the monitor 3. In addition, the generated image data is recorded in a recording medium, as needed.

The endoscope 10 is removably connected to (attached to) the processor-side connector 12 of the processor device 11 for the endoscope, by the scope-side connector 18. In the endoscope system 1 of the present embodiment, when the scope-side connector 18 of the endoscope 10 is attached to the processor-side connector 12 of the processor device 11 for the endoscope, an internal circuit of the endoscope 10 is connected to an internal circuit of the processor device 11 for the endoscope by a non-contact type device such as a transformer and a photo coupler, through the scope-side connector 18 and the processor-side connector 12. Electric insulation is secured between the internal circuit of the endoscope 10 and the internal circuit of the processor device 11 for the endoscope. In other words, the endoscope system 1 is configured so as to be capable of achieving the optical communication of control signals, the non-contact power feeding of the electric power, and the optical communication of image signals.

A non-contact power supply section 82 is structured so as to include the power feeding section 62 in the processor device 11 for the endoscope and the power receiving section 36 in the endoscope 10, and an electric power required for driving the internal circuit of the endoscope 10 is supplied by the non-contact power supply section 82 from the processor device 11 for the endoscope. The power receiving section 36 is arranged in the scope-side connector 18 of the endoscope 10, and the power feeding section 62 is arranged in the processor-side connector 12 of the processor device 11 for the endoscope.

The non-contact power supply device is a device which transmits and receives the electric power in a non-contact manner using electromagnetic coupling. When the scope-side connector 18 of the endoscope 10 is attached to the processor-side connector 12 of the processor device 11 for the endoscope, the power feeding section 62 and the power receiving section 36 are closely arranged to each other at a distance at which the power feeding section 62 and the power receiving section 36 can be electromagnetically coupled so that the electric power can be fed to the power receiving section 36 from the power feeding section 62 in a non-contact manner. The power feeding section 62 is connected to a commercial power source 100 in the outside of the processor device 11 for the endoscope, through a power source stabilizer control section 63. The electric power which has been supplied from the commercial power source 100 and has been stabilized by the power source stabilizer control section 63 is supplied to the power feeding section 62. Due to the electric power that is supplied from the power source stabilizer control section 63 to the power feeding section 62, the electric power is fed from the power feeding section 62 to the power receiving section 36, in a non-contact manner. The power receiving section 36 receives the electric power from the power feeding section 62 in a non-contact manner.

It is preferable that the power feeding section 62 is a primary coil (power feeding coil) which is connected to the power source 100, and that the power receiving section 36 is a secondary coil (power receiving coil) which is electromagnetically coupled to the primary coil. A structure of the primary coil and the secondary coil includes, for example, a structure having: a substrate with a flat surface; and a coil which is wound in a spiral shape around the flat surface.

Incidentally, as for the non-contact power supply device, the example has been described in which the primary coil is used as the power feeding section 62 and the secondary coil is used as the power receiving section 36, in the embodiment, but a device of any type is acceptable as long as the device can transmit and receive the electric power in a non-contact manner.

Here, the electromagnetic coupling means that the two coils are in the state in which an electric power can be sent to one (secondary coil) of the two coils with the use of a magnetic field which is generated when an electric current is passed into the other (primary coil) of the two coils.

The endoscope 10 has a power source generating section 32 that is connected to the power receiving section 36. The power source generating section 32 generates various types of driving power sources required for the internal circuit including the image pickup section 30 and the like, and supplies the generated power source to the internal circuit. For instance, an electric current that is induced in the power receiving section 36 is input to the power source generating section 32, and the power source generating section 32 generates a driving power source from the input electric current which is to be supplied to the internal circuit including the image pickup section 30, a CPU (Central Processing Unit) 46 and the like.

On the distal end portion 14 of the endoscope 10, the image pickup section 30 is arranged. The image pickup section 30 is a device that converts an optical image of the observation site, which has been taken in through the observation window and has been formed by the objective optical system as has been described above, into an electric signal, and outputs the converted electric signal as the image signal. It is preferable for the image pickup section 30 to use a solid-state image pickup element, for instance, such as a CCD (Charge Coupled Device) image sensor and a CMOS (Complementary Metal Oxide Semiconductor) image sensor.

In the present embodiment, the endoscope 10 and the processor device 11 for the endoscope transmit and receive the image signals therebetween by non-contact optical communication. The image signal that is output from the image pickup section 30 is transmitted from the scope-side connector 18 of the endoscope 10 through the processor-side connector 12 of the processor device 11 for the endoscope, to the processor device 11 for the endoscope by optical communication in a non-contact manner.

In the present embodiment, in order to process the image signal sent from the image pickup section 30, there are provided: an AD converter (Analog-Digital converter) 34; a DSP (Digital Signal Processor) 38; a timing signal generating circuit (TSG: Timing Signal Generator) 44; and the like. The image signal sent from the image pickup section 30 is converted from an analog signal into a digital signal, by the AD converter 34. The image signal which has been output from the AD converter 34 is transmitted to the DSP 38. The DSP 38 subjects the image signal sent from the AD converter 34 to necessary processes such as amplification, gamma correction and white balance.

The endoscope 10 and the processor device 11 for the endoscope have, for instance, the following structure, so as to perform the non-contact optical communication therebetween. In the endoscope 10, there are provided: an endoscope-side digital interface (DI: Digital Interface) 40 that is connected to the DSP 38; and an image signal transmission section 42 that is connected to the endoscope-side DI 40. The image signal which has been processed by the DSP 38 is transmitted to the image signal transmission section 42 through the endoscope-side DI 40. The image signals sent from the image pickup section 30 are subjected to the processes, and the optical signals are transmitted to the processor device 11 for the endoscope from the image signal transmission section 42, according to the processed image signals. The image signal transmission section 42 may be a light-emitting device that can emit light for the optical communication, and is preferably, for instance, a laser-emitting element, a light-emitting diode or the like. The laser-emitting element means an element that emits a laser beam which is a coherent light, and the laser beam is preferably a gas laser, a solid-state laser, a semiconductor laser or the like.

The processor device 11 for the endoscope includes: an image signal reception section 64 that receives optical signals from the image signal transmission section 42; a processor-side digital interface 70 (DI: Digital Interface) that is connected to the image signal reception section 64; and a signal processing circuit 72 that is connected to the processor-side DI 70 and functions as the image processing section and the output section. The image signal reception section 64 is a light-receiving device that converts the received optical signal into the electric signal, and is preferably, a light-receiving element such as a semiconductor device or the like, for instance, a photodiode, a phototransistor and the like. The image signal, which has been optically received and converted into the electric signal by the image signal reception section 64, is converted into an image signal for display by the signal processing circuit 72 through the processor-side DI 70, and is output to the monitor 3. In addition, the signal processes such as the gamma correction and the white balance processing are not limited to the case of being performed by the DSP 38 of the endoscope 10, but may be performed by the signal processing circuit 72 of the processor device 11 for the endoscope.

In the present embodiment, the image signal transmission section 42 and the image signal reception section 64 constitute the optical communication section 84 for optically communicating the image signal. As is described later, a window that is an optical member is arranged in an optical path between the image signal transmission section 42 and the image signal reception section 64, in other words, an optical path of the optical communication section 84.

When the scope-side connector 18 of the endoscope 10 is attached to the processor-side connector 12 of the processor device 11 for the endoscope, the image signal transmission section 42 and the image signal reception section 64 are closely arranged to each other at a distance at which the sections can optically communicate with each other so as to set at a state in which the image signal reception section 64 can optically communicate with the image signal transmission section 42 in a non-contact manner.

The endoscope 10 and the processor device 11 for the endoscope transmit and receive the control signals therebetween by the non-contact optical communication. The TSG 44 and the CPU 46 are connected to the image pickup section 30. The TSG 44 and the CPU 46 output a driving signal necessary for the image pickup section 30 to acquire the image signal, to the image pickup section 30. An endoscope-side communication interface (CI: Communication Interface) 48 and a scope-side signal transception section 50 are connected to the CPU 46. The scope-side signal transception section 50 is a device that optically transmits and receives the control signals between the endoscope 10 and the processor device 11 for the endoscope, in a non-contact manner. The scope-side signal transception section 50 includes a light-emitting device that optically transmits the control signal to the processor device 11 for the endoscope as the optical signal, and a light-receiving device that receives the control signal sent from the processor device 11 for the endoscope, as the optical signal. Examples of the scope-side signal transception section 50 may include a device which comprises an infrared-emitting element which optically transmits (infrared rays) signals and a light-receiving element (photodiode, phototransistor or the like) that optically receives signals, and can perform optical communication in a non-contact manner with an IrDA (Infrared Data Association). Accordingly, at least the scope-side signal transception section 50 is arranged in the scope-side connector 18 of the endoscope 10. Another device, for instance, an endoscope-side CI 48 or the like may be arranged in the scope-side connector 18 of the endoscope 10.

The processor device 11 for the endoscope includes: a processor-side signal transception section 66 that optically transmits and receives the control signals to and from the scope-side signal transception section 50 of the endoscope 10; and a processor-side communication interface (CI: Communication Interface) 74 that is connected to the processor-side signal transception section 66. The processor-side signal transception section 66 is a device that can optically transmit and receive the control signals between the endoscope 10 and the processor device 11 for the endoscope. As the processor-side signal transception section 66 includes, for instance: a light-emitting device that optically transmits the control signal to the endoscope 10, as the optical signal; and a light-receiving device that receives the control signal sent from the endoscope 10, as the optical signal. Examples of the processor-side signal transception section 66 of the processor device 11 for the endoscope may include a device which comprises an infrared-emitting element which optically transmits (infrared rays) signals different from those of the scope-side signal transception section 50 of the endoscope 10 and a light-receiving element (photodiode, phototransistor, and the like) that optically receives signals different from those of the scope-side signal transception section 50, and can perform optical data communication in a non-contact manner with an IrDA. The infrared rays generally mean electromagnetic waves that have a wavelength of 0.7 µm to 1 mm.

When the scope-side connector 18 of the endoscope 10 is attached to the processor-side connector 12 of the processor device 11 for the endoscope, the scope-side signal transception section 50 and the processor-side signal transception section 66 are closely arranged to each other at a distance at which the sections can optically communicate with each other. In the present embodiment, the optical communication section 86 is composed of the scope-side signal transception section 50 and the processor-side signal transception section 66, and is set at a state in which the scope-side signal transception section 50 and the processor-side signal transception section 66 can optically communicate with each other. As is described later, a window that is an optical member is arranged in an optical path between the scope-side signal transception section 50 and the processor-side signal transception section 66, in other words, an optical path of the optical communication section 86.

Here, the optical communication section means a structure which contains the optical transmission section and the optical reception section for executing communication using the electromagnetic waves.

The processor device 11 for the endoscope has a light source 68 provided therein. The light source 68 is preferably, for instance, a semiconductor device such as a xenon lamp, a laser diode and a light-emitting diode. The endoscope 10 has a light guide 52 provided therein. On the end of the light guide 52, the light guide rod 20 is provided that is concatenated to the light guide 52. The light guide rod 20 projects from the scope-side connector 18, and is connected to the processor-side connector 12 of the processor device 11 for the endoscope. When the scope-side connector 18 of the endoscope 10 is connected to the processor-side connector 12 of the processor device 11 for the endoscope, the light guide rod 20 and the light source 68 are aligned, and the light emitted from the light source 68 is transmitted to the distal end portion 14 through the light guide rod 20 and the light guide 52.

The processor device 11 for the endoscope includes: a control section 76; and an input section 80 that contains an operation switch, an inspection start switch, a keyboard, a mouse and the like. The control section 76 collectively controls the whole endoscope system 1, in response to the operation of an operator, which is input from the input section 80.

For instance, the control section 76 controls the power feeding section 62, the light source 68, the processor-side DI 70 and the like. In addition, the control section 76 sends a control signal for controlling an imaging operation and the like to the CPU 46 and the like that constitute an internal circuit of the endoscope 10, and controls the whole endoscope system 1.

Furthermore, the control section 76 transmits the control signal which instructs on or off of the power source of the processor device 11 for the endoscope, and the like, to the CPU 46 of the endoscope 10 through the optical communication section 86 based on an instruction that is input by the user (operator) through the input section 80.

The control signal sent from the CPU 46 of the endoscope 10 is transmitted to the control section 76 of the processor device 11 for the endoscope through the optical communication section 86 and the processor-side CI 74, and the control section 76 controls the processor device 11 for the endoscope, in response to the control signal.

Furthermore, in the present embodiment, the control section 76 controls the operation of the removing section for removing the dirt such as a water droplet, fogging and dust, which has been adhered on the window that is an optical member, which is described later.

[Removing Section]

The endoscope system of the present embodiment has a removing section provided therein that removes the dirt such as a water droplet, fogging and dust, which has been adhered on the optical member that is arranged on the optical path of the optical communication section. Accordingly, the endoscope system of the present embodiment makes the removing section remove the dirt such as a water droplet, fogging and dust, which has been adhered on the optical member, and thereby can perform excellent optical communication between the endoscope and the processor device for the endoscope. Here, the dirt means a substance such as the water droplet, fogging and dust, that causes lowering of the optical signal when it adheres on the optical member.

First Embodiment

Figure 3:
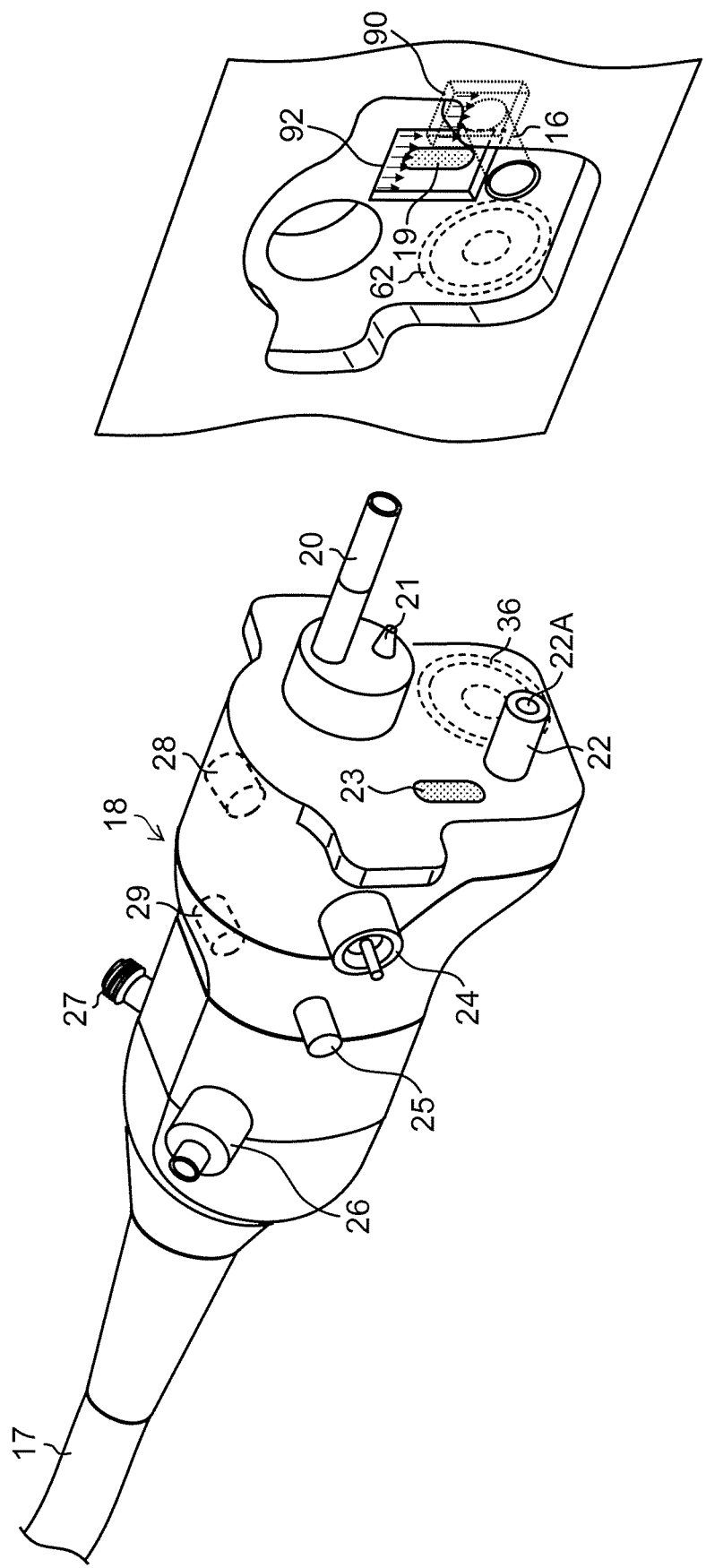
FIG. 3 is a perspective view that enlarges a scope-side connector and a processor-side connector according to a first embodiment.
Figure 4:
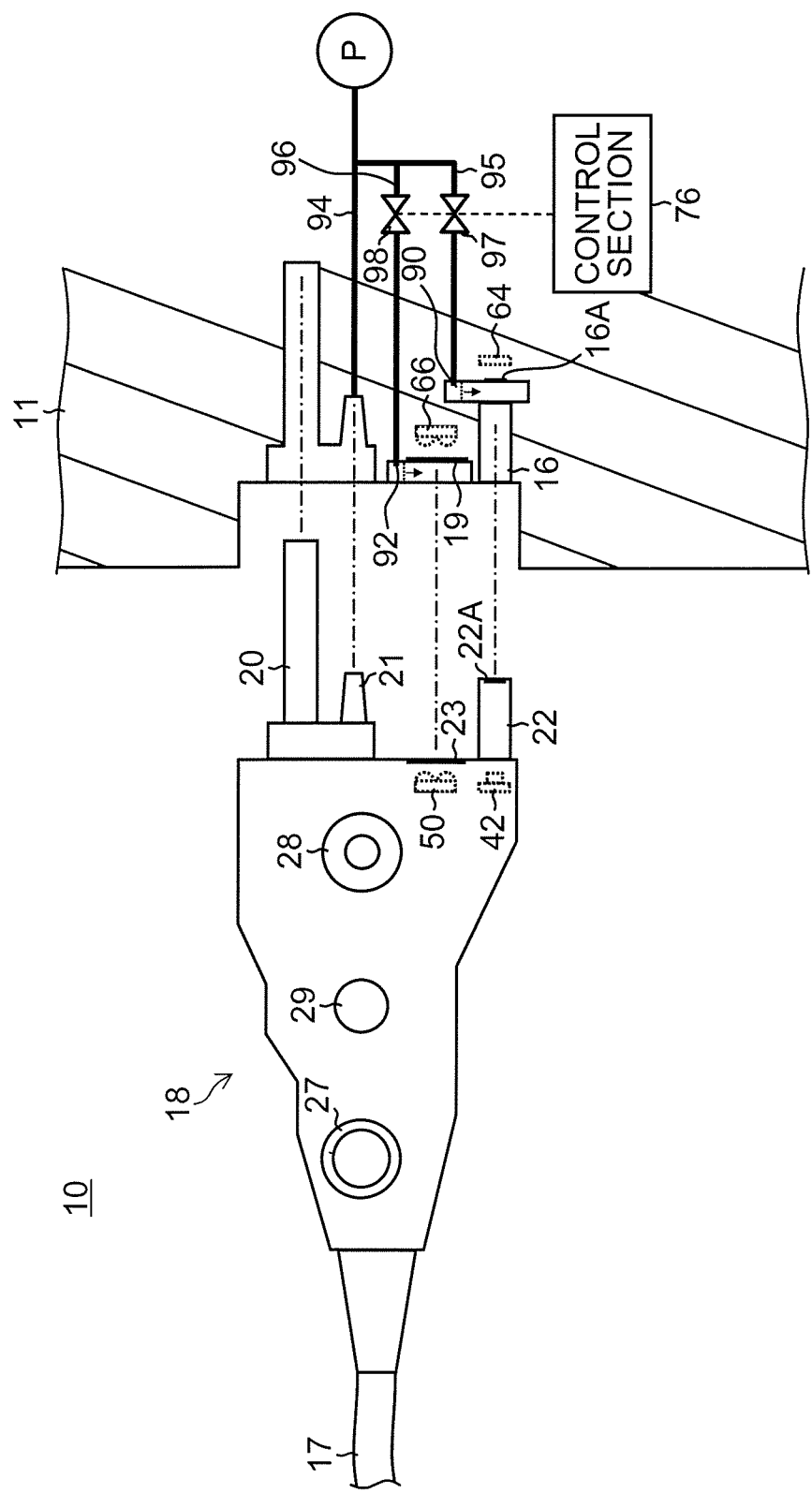
FIG. 4 is a cross-sectional view that enlarges the scope-side connector and the processor-side connector according to the first embodiment.

The removing section of the first embodiment is described below with reference to the drawings. FIG. 3 is a perspective view that enlarges a scope-side connector and a processor-side connector; and FIG. 4 is a cross-sectional view that enlarges the scope-side connector and the processor-side connector.

As has been described above, the feed and reception of an electric power, the transmission and reception of image signals and the bidirectional transmission and reception of control signals are performed between the endoscope 10 and the processor device 11 for the endoscope in a non-contact manner.

Accordingly, it is not necessary to provide an electric contact point on the scope-side connector 18, which is to be directly connected to the processor device 11 for the endoscope. The scope-side connector 18 can be formed into a waterproof structure that is covered with a resin which has electrically insulative properties and is excellent in chemical resistance. By being formed into the waterproof structure, the scope-side connector 18 can protect electric components and the like which are arranged inside of the scope-side connector 18, from cleaning water and the like, without attaching an additional waterproof cap thereon, in cleaning and disinfecting operations.

As is shown in the figures, the scope-side connector 18 includes: a light guide rod 20 that projects toward the processor-side connector 12; a shaft 22; and an air feed fitting 21. The air feed fitting 21 communicates with an air/water feed pipeline that is arranged in the endoscope 10 for sending air and water up to the distal end portion 14 of the endoscope 10.

The scope-side connector 18 is formed to have a hollow structure that has an internal space. Of the internal space of the scope-side connector 18, in a space which is close to the processor-side connector 12, there are arranged: a power receiving section 36; an image signal transmission section 42; and a scope-side signal transception section 50.

In the processor-side connector 12, a power feeding section 62 is arranged at a position corresponding to the power receiving section 36, an image signal reception section 64 is arranged at a position corresponding to the image signal transmission section 42, and a processor-side signal transception section 66 is arranged at a position corresponding to the scope-side signal transception section 50.

The shaft 22 that projects from the scope-side connector 18 is used for aligning the image signal transmission section 42 of the endoscope 10 with the image signal reception section 64 of the processor device 11 for the endoscope. It is preferable that the image signal transmission section 42 is accurately fixed to the shaft 22, and the image signal transmission section 42 is arranged in an extending direction of the central axis of the shaft 22. Furthermore, a window 22A for the image signal, which is formed of the optical member, is provided on the distal end of the shaft 22 so as to pass the optical signal that is sent from the image signal transmission section 42 therethrough.

The image signal reception section 64 is accurately fixed to a hole 16 of the processor-side connector 12, into which the shaft 22 is inserted. Furthermore, a window 16A for an image signal, which is formed of an optical member, is provided on the bottom side of the hole 16, so as to pass the optical signal therethrough that has been sent from the image signal transmission section 42, to the image signal reception section 64.

The shaft 22 is inserted into the hole 16, and thereby the image signal transmission section 42 is accurately aligned with the image signal reception section 64. The image signal is optically transmitted from the image signal transmission section 42 to the image signal reception section 64 through the window 22A and the window 16A that are arranged in the optical path (optical path of optical communication section 84) between the image signal transmission section 42 and the image signal reception section 64.

At a position corresponding to the scope-side signal transception section 50, a window 23 for the control signal, which is formed of the optical member, is provided on the scope-side connector 18. In addition, at a position corresponding to the processor-side signal transception section 66, a window 19 for the control signal, which is formed of the optical member, is provided on the processor-side connector 12.

The control signal is bidirectionally and optically communicated between the scope-side signal transception section 50 and the processor-side signal transception section 66, through the window 23 and the window 19 that are arranged in the optical path (optical path of optical communication section 86) between the scope-side signal transception section 50 and the processor-side signal transception section 66.

The optical path means a path through which the optical signal passes when sections optically communicate with each other in a non-contact manner. In addition, the optical member is a member that can pass a light therethrough, and includes a flat plate, a lens and a filter which are made from glass or resin.

The power receiving section 36 is arranged in the space inside of the scope-side connector 18, and accordingly is not exposed to the outside.

An air/water feed connector 24 is provided on the side face of the scope-side connector 18. The air/water feed connector 24 is connected to a water feed tank (not shown). The operator can feed a gas (for instance, air) or a liquid (for instance, water) to the distal end portion 14, by operating an air/water feed button of the operation section 15. The dirt on the lens surface of the distal end portion 14 is removed by water that is supplied to the distal end portion 14. In addition, with the air supplied to the distal end portion 14, a lumen of a patient is expanded or the water droplet on the lens is removed.

In addition, a suction connector 28 is arranged on the side face in an opposite side of the air/water feed connector 24 of the scope-side connector 18. By being connected with a tube, the suction connector 28 can communicate with a suction device (no shown). By operating the suction button of the operation section 15 in a state in which the suction device is driven, the operator can make the suction device suck a lesioned part and the like through a forceps port of the distal end portion 14.

In the present embodiment, the suction connector 28 is provided on the side face in an opposite side of the image signal transmission section 42, when the scope-side connector 18 is viewed from the insertion direction. In other words, the suction connector 28 is arranged on the side face that is farther from the shaft 22. Due to this configuration, even in the case where the lesioned part flies out from the suction connector 28, for instance, when the tube is removed from the suction connector 28, it can be suppressed that the window 22A of the shaft 22 becomes dirty. On the other hand, because the suction connector 28 is arranged on the side face that is close to the power receiving section 36, there may be a case where the lesioned part which flies out from the suction connector 28 is adhered on the power receiving section 36. A region of the scope-side connector 18, on which the power receiving section 36 is arranged, is formed of a flat surface, and accordingly can be easily cleaned by a wipe or the like.

On the side face of the scope-side connector 18, a balloon connector 25 is further provided. When the tube is connected to the balloon connector 25, a balloon (not shown) that is provided in the insertion section 13 can be expanded or shrunk. In the case of the endoscope 10 in which the balloon is not provided in the insertion section 13, it is not necessary to provide the balloon connector 25 on the scope-side connector 18.

A sub water feed connector 29 is arranged on the side face in an opposite side of the balloon connector 25 of the scope-side connector 18. A tube is connected with the sub water feed connector 29, and thereby can feed water to the distal end portion 14 of the endoscope 10 therethrough. A dirty substance adhered on a body cavity, the blood flowed out by endoscopic surgery, and the like are washed by the water that id supplied to the distal end portion 14 through the sub water feed connector 29.

Incidentally, the scope-side connector 18 may have at least one of the balloon connector 25 and the sub water feed connector 29.

An aeration connector 26 is provided on the side face of the scope-side connector 18. The aeration connector 26 is used for a leak test that inspects an air leakage of the insertion section 13.

In addition, an S-type connector 27 is arranged on the side face in an opposite side of the aeration connector 26 of the scope-side connector 18. The S-type connector 27 can detect a leakage of high frequency current, and when the leakage is detected, the S-type connector can notify the leakage and automatically stop the output of the high frequency current. The S-type connector 27 is a terminal to which an S-code is connected that is used, for instance, for returning a high-frequency electric current which has leaked to the endoscope 10, to the control section of an electric operation device when the electric operation device (electric cautery) is used.

The scope-side connector 18 may have at least one of the aeration connector 26 and the S-type connector 27.

A cover rubber is arranged so as to cover the rear end portion of the scope-side connector 18, and the universal cord 17 projects from the cover rubber.

In the endoscope system 1, it is necessary to clean and disinfect the endoscope 10 after use. There is a case where the deposition of a water droplet and dirt such as fogging and dust occurs on the window 22A and the window 23 due to cleaning and disinfection, which are the optical members existing in the side of the endoscope 10. By the influence of the dirt, the optical signal is weakened when passing through the window 22A and the window 23 so that the reception sensitivity is lowered and disturbance occurs on the signal. Thereby, there is a possibility that optical communication cannot be performed. In addition, there is a case where the dirt that has been adhered on the window 22A and the window 23 affects the window 16A and the window 19 that are the optical members in the processor-side connector 12 of the processor device 11 for the endoscope. Accordingly, it is necessary to remove the dirt that has been adhered on the window 22A, the window 23, the window 19 and/or the window 16A.

In the endoscope system 1 of the present embodiment, the removing section for removing the dirt is provided. Two air blowing sections (first air blowing section 90 and second air blowing section 92) are provided as the removing section. The first air blowing section 90 is arranged in the periphery of the window 16A corresponding to the image signal reception section 64 in the side of the processor-side connector 12. When the shaft 22 is inserted into the hole 16, the first air blowing section 90 can blow gas to the window 22A of the shaft 22 and the window 16A of the processor-side connector 12. The first air blowing section 90 can be formed, for instance, of a nozzle or the like, which has a spout for feeding the gas toward the window 22A and the window 16A therethrough. As long as the air blowing section can blow the gas toward the window 22A and the window 16A, the structure and the like are not limited.

The first air blowing section 90 can remove the dirt that has been adhered on the window 22A and/or the window 16A, by blowing the gas toward the window 22A and/or the window 16A therefrom.

The second air blowing section 92 is arranged in the periphery of the window 19 corresponding to the processor-side signal transception section 66 in the side of the processor-side connector 12. When the scope-side connector 18 and the processor-side connector 12 are connected to each other, the second air blowing section 92 can feed gas to the window 23 of the scope-side connector 18 and the window 19 of the processor-side connector 12. The second air blowing section 92 can be formed, for instance, of a nozzle or the like, which has a spout for feeding the gas toward the window 23 and the window 19 therethrough. As long as the air blowing section can blow the gas toward the window 23 and the window 19, the structure and the like are not limited.

The second air blowing section 92 can remove the dirt that has been adhered on the window 23 and/or the window 19, by blowing the gas toward the window 23 and/or the window 19 therefrom.

In the present embodiment, the two air blowing sections (first air blowing section 90 and second air blowing section 92) are illustrated, but it is acceptable to have at least one air blowing section provided therein. In particular, the influence of the dirt is large between the image signal transmission section 42 and the image signal reception section 64. Accordingly, it is preferable to provide at least the first air blowing section 90.

Next, the gas feed to the two air blowing sections (first air blowing section 90 and second air blowing section 92) is described below.

Generally, in the endoscope system 1, the endoscope 10 has a feed path for the pressurized liquid and gas. The pressurized liquid is used for various purposes such as cleaning of an observation window, cleaning of an inner wall of a body cavity, spraying of a chemical liquid, and further the perfusion of passing a liquid to an organ or a tissue. The pressurized gas is used for the purposes such as expansion of the inside of the body cavity and removal of the droplet on the observation window after cleaning.

As a gas feeding section that serves as a pressurizing source for these liquid and gas, a pump P is usually provided in the processor device 11 for the endoscope. When the pump P is driven, the pressurized gas is supplied to the endoscope 10 through a gas pipeline 94 and an air feed fitting 21.

By blocking a hole of the air/water feed button (not-shown) on the operation section of the endoscope 10, the distal end is connected to the pump in a pipeline (not-shown), and the gas can be blown from the distal end portion 14 of the endoscope. In addition, when the air/water feed button is pushed, the air feed pipeline (not-shown) is blocked, and the gas flows into the water feed tank (not-shown). The gas pushes out the liquid in the water feed tank, the liquid flows in the pipeline, and the liquid can be blown from the distal end.

The endoscope system in the present embodiment uses the pump P that is provided on the processor device 11 for the endoscope in order to feed the gas to the air blowing sections (first air blowing section 90 and second air blowing section 92). By using the pump P that is provided in the processor device 11 for the endoscope, the endoscope system does not need to provide a separate gas feeding section for the air blowing section.

As is shown in the figure, the gas pipeline 94 is branched to a first pipeline 95 and a second pipeline 96. The first pipeline 95 and the first air blowing section 90 communicate with each other. In addition, the second pipeline 96 and the second air blowing section 92 communicate with each other. Valves 97 and 98 are provided in the first pipeline 95 and the second pipeline 96, respectively. By opening or closing the valves 97 and 98, the processor device can control the feed of the gas to the first air blowing section 90 and the second air blowing section 92. The valves 97 and 98 are electrically connected to the control section 76. The opening and closing of the valves 97 and 98 can be controlled based on the control signal of the control section 76.

Next, a flow for controlling the operation of the removing section for the optical member is described. In the first control flow, the control section can detect that the processor-side connector 12 and the scope-side connector 18 have been connected to each other, and control the removing section.

In the present embodiment, the control section detects that the processor-side connector 12 and the scope-side connector 18 have been connected to each other, and makes the air blowing sections (first air blowing section 90 and second air blowing section 92) that serve as the removing section to blow gas toward the optical members (windows 16A and 22A, and windows 23 and 19).

The removing section removes the dirt when the processor-side connector 12 and the scope-side connector 18 are connected to each other, and thereby can remove the dirt from the optical member before the endoscope system 1 is used.

Figure 5:
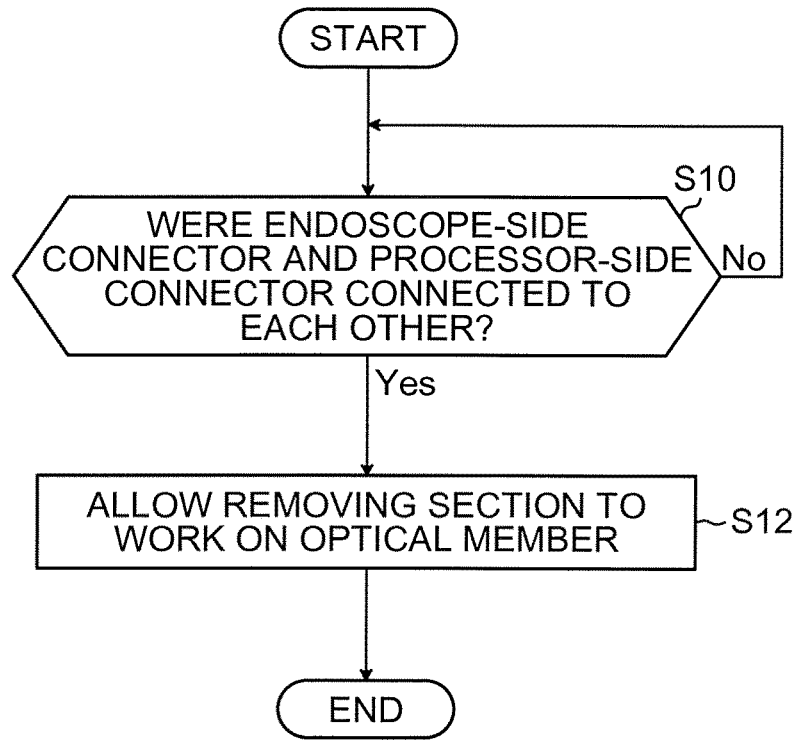
FIG. 5 is a flow chart showing a first control flow of a removing section.

FIG. 5 is a flow chart showing the first control flow of the removing section. In FIG. 5, the control section 76 detects whether or not the processor-side connector 12 and the scope-side connector 18 are connected to each other (step S10), and when the processor-side connector 12 and the scope-side connector 18 are connected to each other (detection result is "Yes"), the control section 76 operates (controls) the removing section to work on the optical member (step S12). When air blowing sections serve as the removing section, a gas is blown toward the optical member from the air blowing sections based on the control signal of the control section 76. When the detection result is "Yes", it is preferable to previously set the gas feed amount, the gas pressure, the number of times of blowing and the like of the gas to be blown toward the optical member from the air blowing sections.

The detection concerning whether or not the processor-side connector 12 and the scope-side connector 18 are connected to each other is described below.

For instance, an LG (Light Guide) detection switch (not shown) can be arranged in the vicinity of the processor-side connector 12 of the processor device 11 for the endoscope, to which the scope-side connector 18 of the endoscope 10 is connected.

The LG detection switch detects electrical connection with the light guide rod 20 that is covered with metal, and thereby detects that the light guide rod 20 is inserted (in other words, that processor-side connector 12 and scope-side connector 18 are connected to each other). When the LG detection switch detects the insertion of the light guide rod 20, the LG detection switch outputs the detection signal to the control section 76.

Incidentally, the LG detection switch to be used is not limited to the switch that detects the electrical connection with the light guide rod 20, but may be a microswitch that detects mechanical contact with the light guide rod 20, a photo-interrupter that optically detects the presence or absence of the light guide rod 20, or the like.

When a plurality of LG detection switches are provided, the control section can detect the moving direction of the light guide rod 20. If the control section can detect the moving direction, the control section can detect whether the light guide rod 20 approaches the processor-side connector 12 or moves away therefrom, and can control the removing section at preferable timing.

As for a second control flow of the removing section, the control section can control the removing section based on an input value of the optical communication section. In the present embodiment, a gas is blown toward the optical members (windows 16A and 22A and windows 23 and 19) from the air blowing sections (first air blowing section 90 and second air blowing section 92) that serve as the removing section based on the input values of the optical communication section 84 and the optical communication section 86. The input value of the optical communication section means a value in the reception section of the optical signal in the optical communication section.

The input value that is output from the optical communication sections 84 and 86 is reduced by the dirt that is adhered on the optical member. The threshold value of the optical output has been previously set, and the threshold value and the input value are compared. When the input value is smaller than the threshold value, the gas is blown toward the optical members (windows 16A and 22A and windows 23 and 19) from the air blowing sections (first air blowing section 90 and second air blowing section 92), and the dirt can be removed. The control section can control the air blowing sections according to the degree of the dirt.

Figure 6:
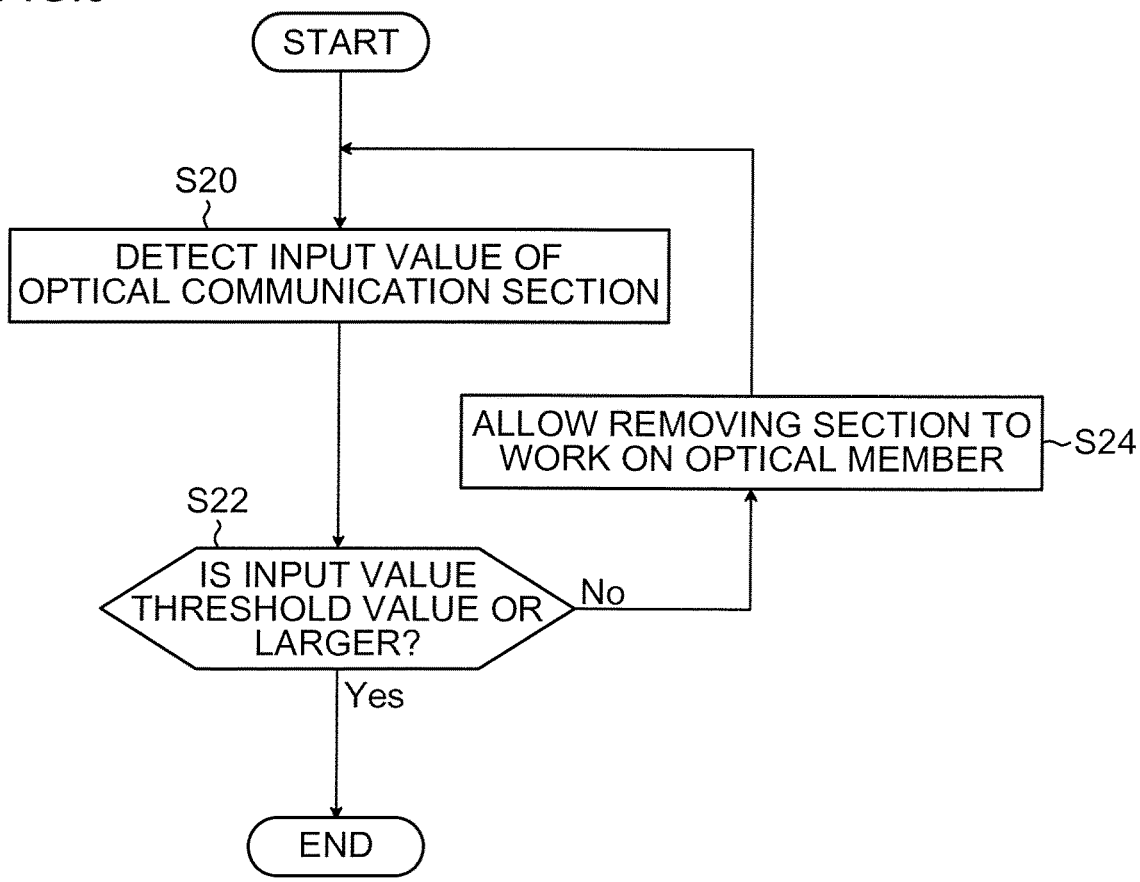
FIG. 6 is a flow chart showing a second control flow of the removing section.

FIG. 6 is a flow chart showing the second control flow of the removing section. In FIG. 6, the control section 76 (or CPU 46) detects the input value from the image signal reception section 64 that constitutes the optical communication section 84, and/or from the scope-side signal transception section 50 or the processor-side signal transception section 66 that constitute the optical communication section 86 (step S20). The control section 76 determines whether or not the input value is equal to or larger than the previously set threshold value (step S22). When the determination result is "No", the control section 76 operates (controls) the removing section to work on the optical member (step S22). When the air blowing sections serve as the removing section, a gas is blown toward the optical member from the air blowing sections based on the control signal of the control section 76. The step S20 and the step S24 are repeatedly executed until the input value becomes equal to or larger than the previously set threshold value.

The second control flow of the second removing section can further include a flow for controlling the output value of the light based on the input value of the optical communication section. The output value (strength) of the light of the optical communication section means a value in the light-emitting section of the optical signal in the optical communication section.

Figure 7:
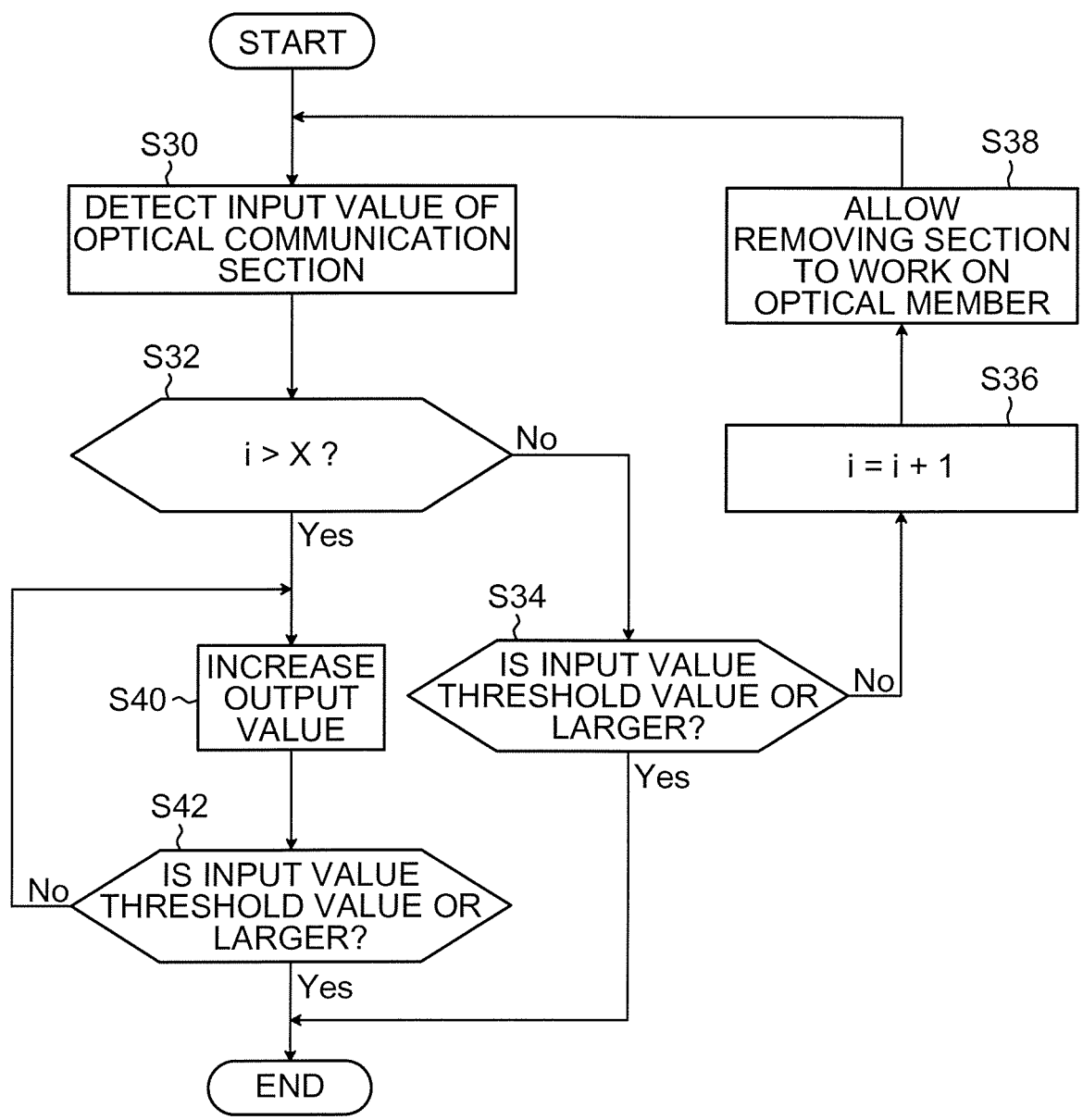
FIG. 7 is a flow chart showing a modified example of the second control flow of the removing section.

FIG. 7 is a flow chart showing another second control flow of the removing section. In FIG. 7, the control section 76 (or CPU 46) detects the input value from the image signal reception section 64 that constitutes the optical communication section 84 and/or the processor-side signal transception section 66 that constitutes the optical communication section 86 (step S30). The control section 76 determines whether or not the number of times i ("i" is an integer which indicates the number of times the removing section has been operated) is larger than the preset X (step S32). When the determination result is "No", the control section 76 determines whether or not the input value is equal to or larger than the previously set threshold value (step S34). When the determination result is "No", the control section 76 replaces the number of times i, at which the removing section has been operated, with a value of "i+1" (step S36). The control section 76 operates (controls) the removing section to work on the optical member (step S38). When air blowing sections serve as the removing section, a gas is blown toward the optical member from the air blowing sections based on the control signal of the control section 76. When the number of times i, at which the removing section has been operated, is equal to the preset X or less, the step S30 to the step S38 are repeatedly executed until the input value becomes equal to or larger than the previously set threshold value.

When the control section 76 determines that the number of times i, at which the removing section has been operated, is larger than the set X (step S32), the control section 76 performs such a control (increasing output value) as to increase the optical outputs of the optical communication sections 84 and/or 86 (step S40). More specifically, the control section 76 increases the output value of the light, by increasing: electric currents for driving the image signal transmission section 42 that constitutes the optical communication section 84, and/or the scope-side signal transception section 50 or the processor-side signal transception section 66 which constitute the optical communication section 86, and the like.

The control section 76 determines whether or not the input value is equal to or larger than the previously set threshold value (step S42). The step S40 and the step S42 are repeatedly executed until the input value becomes equal to or larger than the previously set threshold value.

According to this control flow, in the case where the input value does not become the threshold value or larger even though the removing section has been operated, the input value can be made equal to or larger than the threshold value by increasing the output value. It becomes possible for the endoscope 10 and the processor device 11 for the endoscope to securely perform optical communication therebetween.

Next, a method for detecting the input value of the optical communication section 86 that is constituted by the scope-side signal transception section 50 and the processor-side signal transception section 66 is described below.

Figure 8:
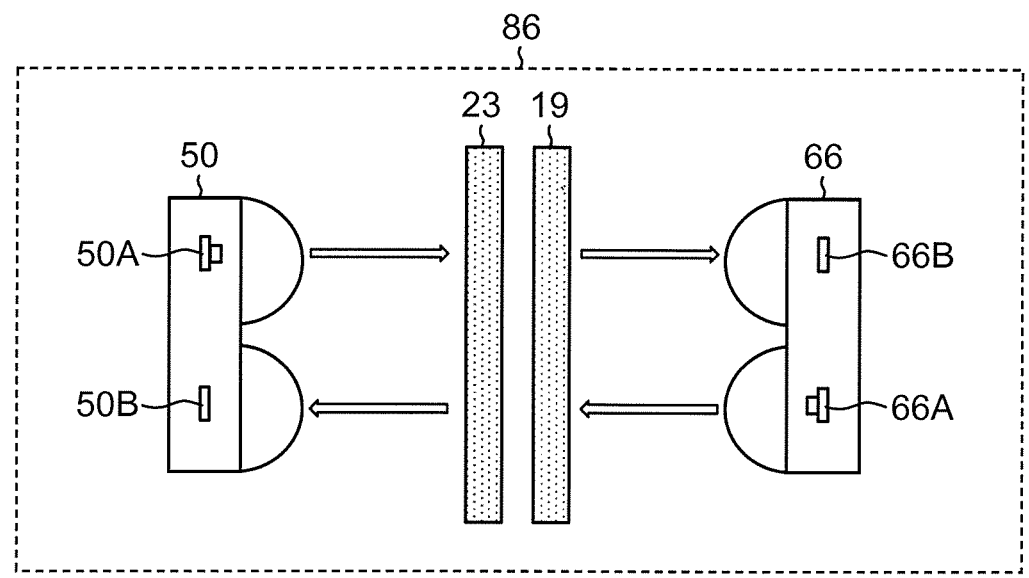
FIG. 8 is a schematic block diagram of an optical communication section that contains a scope-side signal transception section and a processor-side signal transception section.
Figure 9:
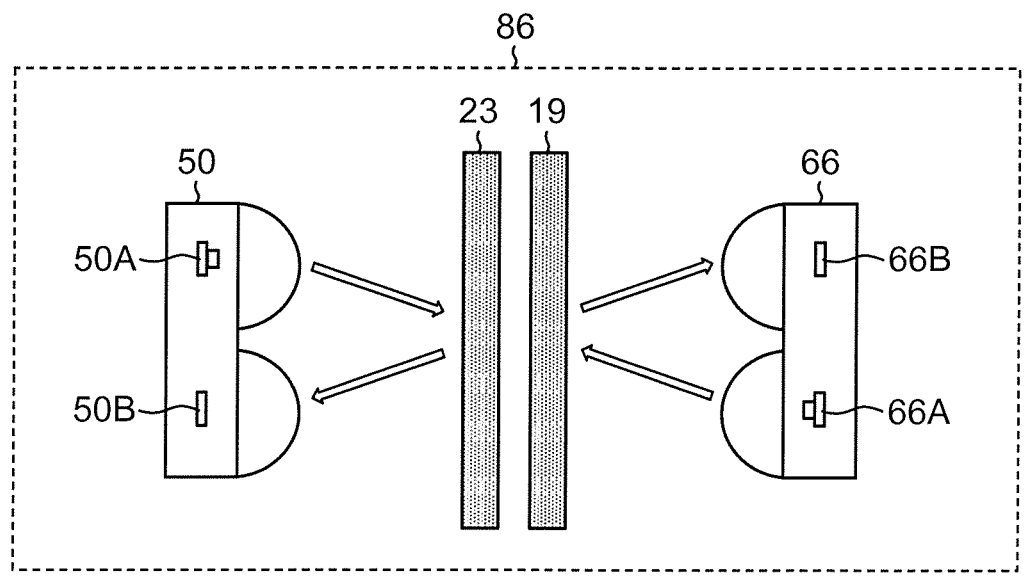
FIG. 9 is a schematic block diagram of an optical communication section that contains the scope-side signal transception section and the processor-side signal transception section.

FIG. 8 and FIG. 9 are schematic block diagrams of the optical communication section 86 that is constituted by the scope-side signal transception section 50 and the processor-side signal transception section 66. As is shown in FIG. 8, the windows 19 and 23 serving as the optical members are disposed between the scope-side signal transception section 50 and the processor-side signal transception section 66. The scope-side signal transception section 50 is provided with a light-emitting element 50A that outputs light and a light-receiving element 50B to which a light is input. In addition, the processor-side signal transception section 66 is provided with a light-emitting element 66A that outputs light and a light-receiving element 66B to which a light is input.

As is shown in FIG. 8, generally, the output light from the light-emitting element 50A of the scope-side signal transception section 50 passes through the windows 19 and 23, and is input into the light-receiving element 66B of the processor-side signal transception section 66. The output light from the light-emitting element 66A of the processor-side signal transception section 66 passes through the windows 19 and 23, and is input into the light-receiving element 50B of the scope-side signal transception section 50.

The control section 76 (or CPU 46) (not shown in FIG. 8) detects whether or not the input values of the light-receiving element 66B and/or the light-receiving element 50B are equal to the previously set threshold values or larger. When the input values are less than the previously set threshold value, the control section 76 operates the air blowing sections serving as the removing section in order to remove the dirt adhered on the windows 19 and/or 23.

Furthermore, the output value of the light-emitting element 50A is controlled according to the determination in the light-receiving element 66B. In addition, the output value of the light-emitting element 66A is controlled according to the determination in the light-receiving element 50B.

FIG. 9 illustrates another method for detecting the input value of the optical communication section 86, which is different from the method in FIG. 8. As is shown in FIG. 8, generally, the control section detects the output value of the light-emitting element 50A as the input value of the light-receiving element 66B, and detects the output value of the light-emitting element 66A as the input value of the light-receiving element 50B. However, the case is considered in which the light does not pass through the windows 19 and/or 23, due to the influence of the dirt on the windows. On the other hand, the light may be reflected by the windows 19 and/or 23.

Then, for instance, as is shown in FIG. 9, the output light from the light-emitting element 50A of the scope-side signal transception section 50 is reflected by the windows 19 and 23, and is input into the light-receiving element 50B of the scope-side signal transception section 50. The output light from the light-emitting element 66A of the processor-side signal transception section 66 is reflected by the windows 19 and 23, and is input into the light-receiving element 66B of the processor-side signal transception section 66.

The control section 76 (or CPU 46) (not-shown in FIG. 9) detects whether or not the input values of the light-receiving element 66B and/or the light-receiving element 50B are equal to the previously set threshold value or larger. When the input values are less than the previously set threshold value, the control section 76 operates the air blowing sections serving as the removing section in order to remove the dirt adhered on the windows 19 and/or 23.

As for a third control flow of the removing section, the control section can control the removing section in response to an operation of a manual switch. In the present embodiment, a gas is blown from the air blowing sections (first air blowing section 90 and second air blowing section 92) which serve as the removing section toward the optical members (windows 16A and 22A and windows 23 and 19) in response to the operation of the manual switch. The dirt can be removed from the optical member at the timing when an operator desires.

Figure 10:
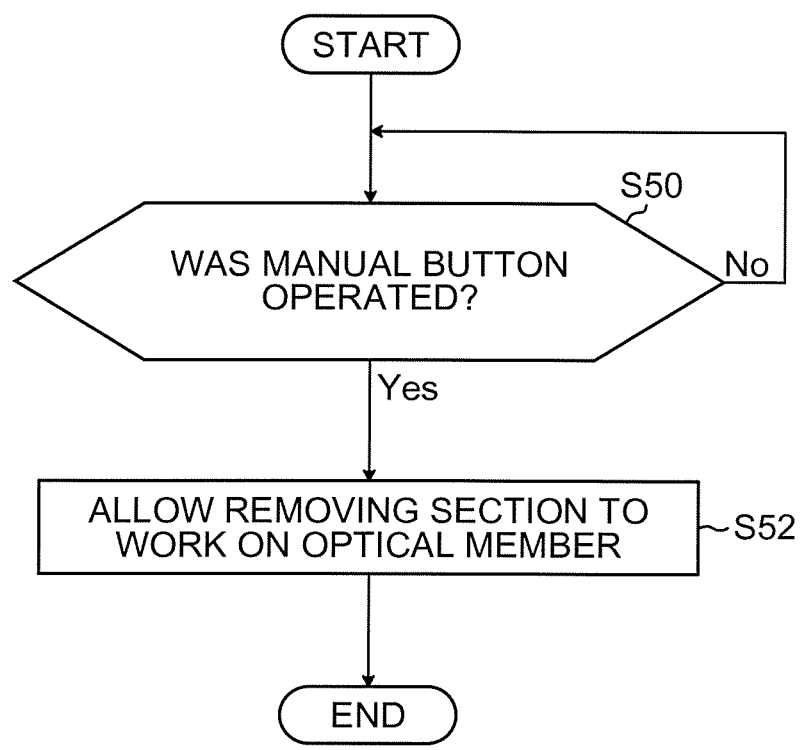
FIG. 10 is a flow chart showing a third control flow of the removing section.

FIG. 10 is a flow chart showing the third control flow of the removing section. In FIG. 10, the control section 76 detects whether or not the manual switch is operated (step S50). When the detection result is "Yes", the control section 76 operates (controls) the removing section to work on the optical member (step S52). When air blowing sections serve as the removing section, a gas is blown toward the optical member from the air blowing sections based on the control signal of the control section 76. When the detection result is "Yes", it is preferable to previously set the gas feed amount, the gas pressure, the number of times of blowing and the like of the gas to be blown toward the optical member from the air blowing sections.

In the present embodiment, the three control flows of the removing section have been described, but the control flow is not limited to the three control flows. In addition, the operation of the removing section can be controlled by any combination of the three control flows.

For instance, the control section can operate the removing section at the time when the processor-side connector 12 and the scope-side connector 18 are connected to each other, and operate the removing section based on the input value of the optical communication section when the endoscope system 1 is used by the operator, and further operate the removing section in response to the operation of the operation button by the operator.

Second Embodiment

Figure 11:
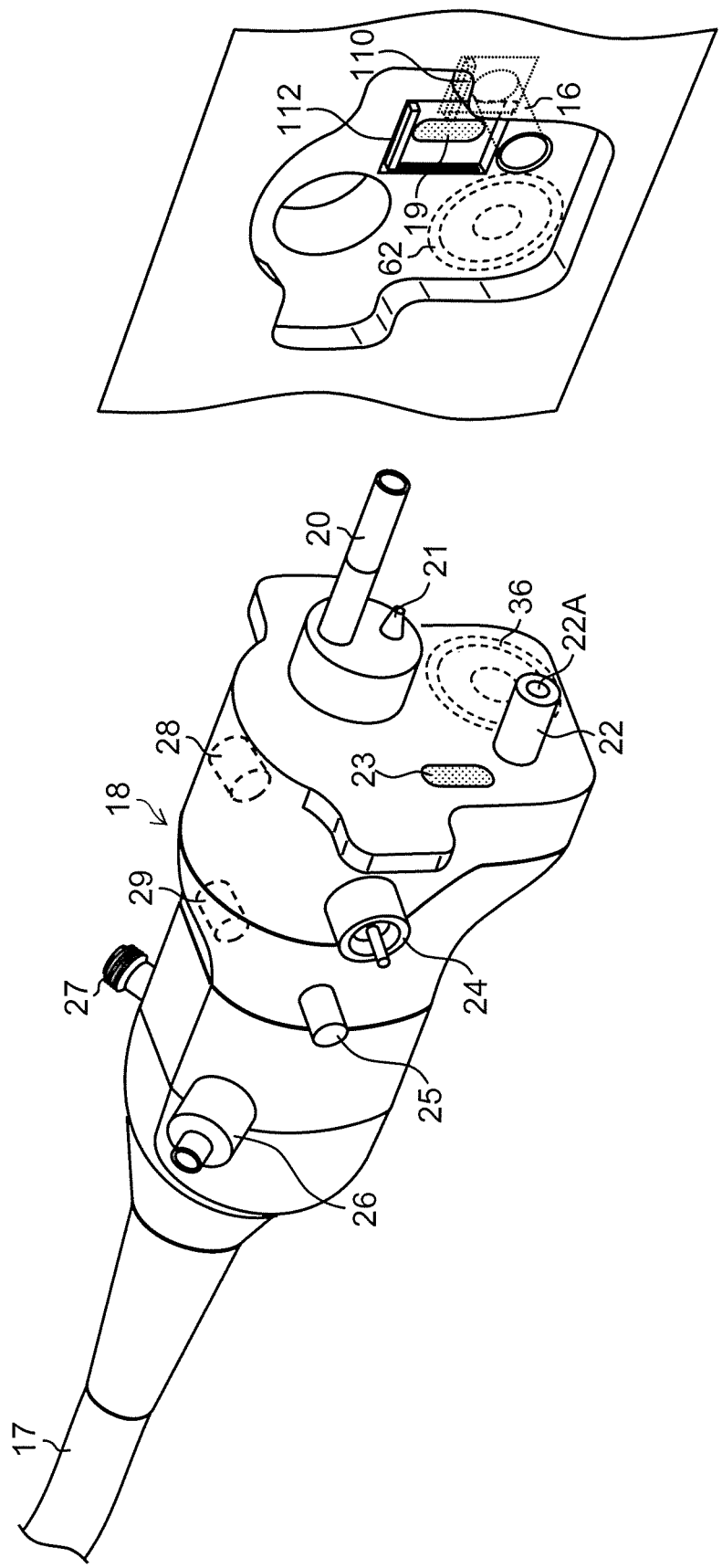
FIG. 11 is a perspective view that enlarges a scope-side connector and a processor-side connector according to a second embodiment.
Figure 12:
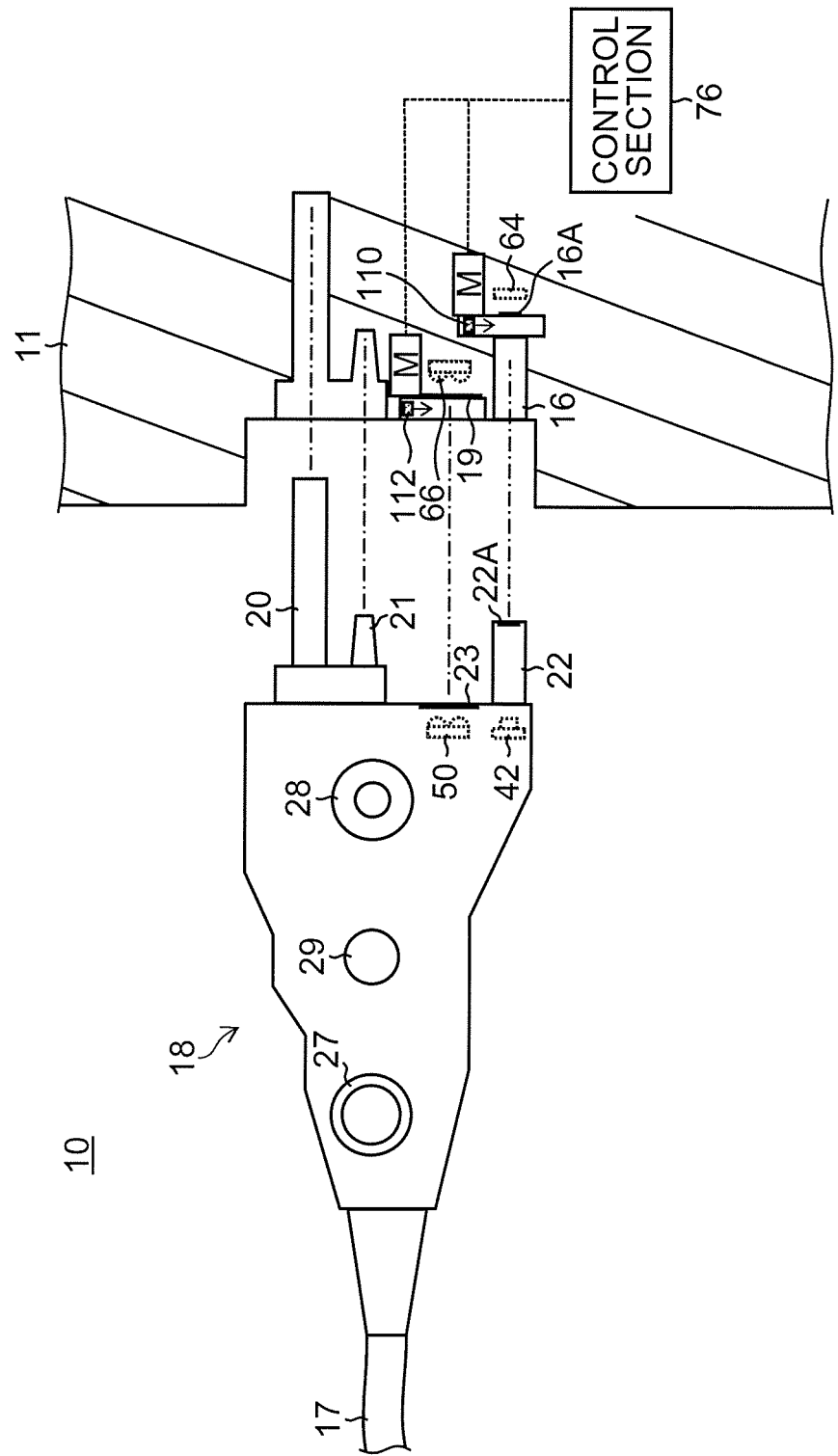
FIG. 12 is a sectional view that enlarges the scope-side connector and the processor-side connector according to the second embodiment.

A removing section according to a second embodiment is described below with reference to the drawings. Incidentally, a configuration similar to that in the first embodiment is designated by the same reference numeral, and the description is occasionally omitted. FIG. 11 is a perspective view that enlarges the scope-side connector and the processor-side connector; and FIG. 12 is a cross-sectional view that enlarges the scope-side connector and the processor-side connector.

In the endoscope system 1 of the present embodiment, there is provided a removing section for removing the dirt such as a water droplet, fogging and dust, which has been adhered on the optical member. Two wiper sections (first wiper section 110 and second wiper section 112) are provided as the removing section.

The first wiper section 110 is arranged in the periphery of the window 16A corresponding to the image signal reception section 64 in the side of the processor-side connector 12. When the shaft 22 is inserted into the hole 16, the first wiper section 110 can wipe the surfaces of the window 22A of the shaft 22 and the window 16A of the processor-side connector 12. The first wiper section 110 includes, for instance, a wiper blade that is made from a resin and has elasticity, and a motor. The wiper blade can be reciprocally moved by driving the motor. As long as the wiper blade can wipe the surfaces of the window 22A and the window 16A, the material, the shape and the like of the wiper blade are not limited.

The first wiper section 110 wipes the surfaces of the window 22A and the window 16A, and thereby can remove the dirt adhered on the window 22A and/or the window 16A.

The second wiper section 112 is arranged in the periphery of the window 19 corresponding to the processor-side signal transception section 66 in the side of the processor-side connector 12. When the scope-side connector 18 and the processor-side connector 12 are connected to each other, the second wiper section 112 can wipe the surfaces of the window 23 of the scope-side connector 18 and the window 19 of the processor-side connector 12. The second wiper section 112 includes, for instance, a wiper blade that is made from a resin and has elasticity, and a motor. The wiper blade can be reciprocally moved by driving the motor. As long as the wiper blade can wipe the surfaces of the window 23 and the window 19, the material, the shape and the like of the wiper blade are not limited.

The second wiper section 112 wipes the surfaces of the window 23 and the window 19, and thereby can remove the dirt adhered on the window 23 and/or the window 19.

In the present embodiment, the two wiper sections (first wiper section 110 and second wiper section 112) have been illustrated, but it is acceptable to have at least one wiper section provided therein. In particular, the influence of the dirt is large between the image signal transmission section 42 and the image signal reception section 64. Accordingly, it is preferable to provide at least the first wiper section 110.

Similarly to the first embodiment, the control section 76 can control the wiper sections (first wiper section 110 and second wiper section 112) that constitute the removing section, according to the three control flows illustrated in FIGS. 4 to 7 and FIG. 9. In addition, the operation of the removing section can be controlled by any combination of the three control flows.

Third Embodiment

Figure 13:
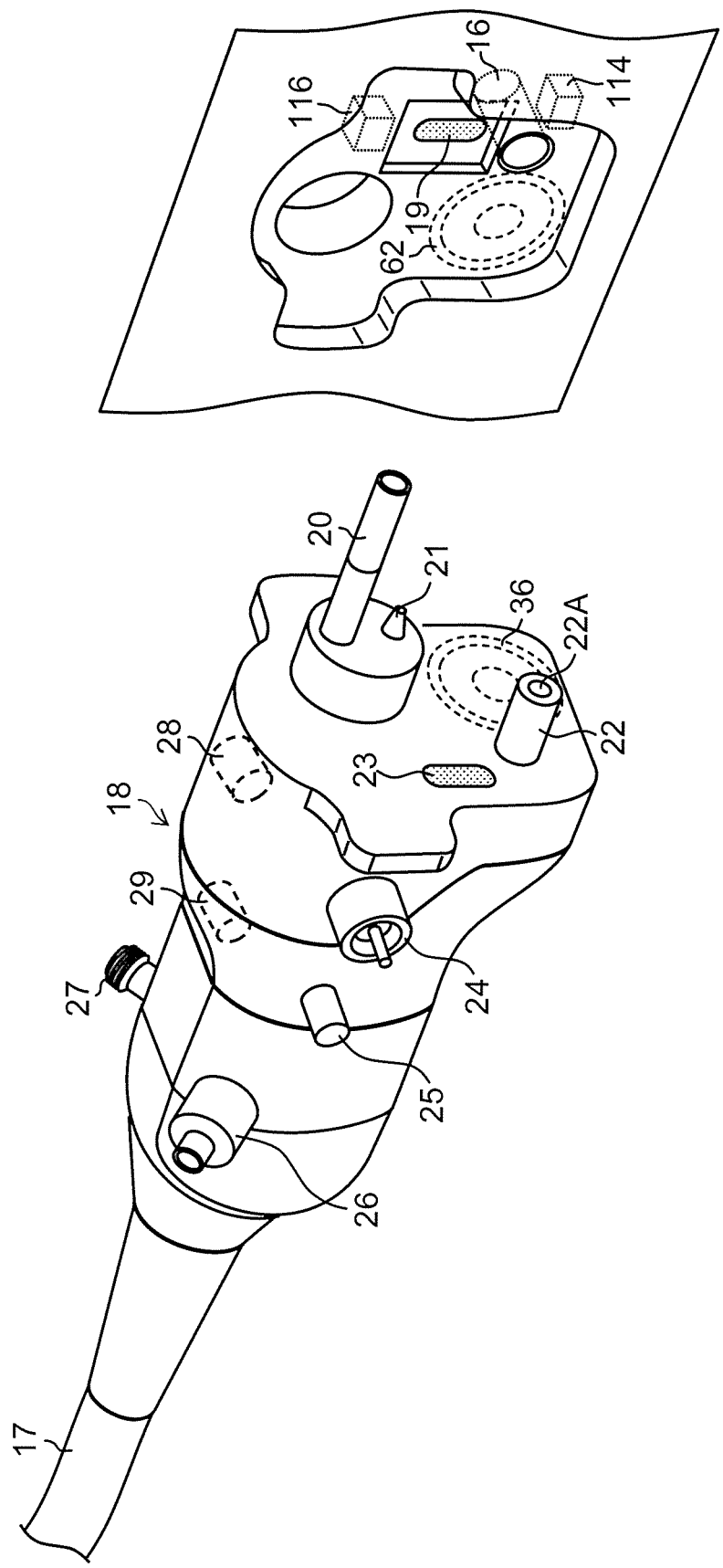
FIG. 13 is a perspective view that enlarges a scope-side connector and a processor-side connector according to a third embodiment.

A removing section according to a third embodiment is described below with reference to the drawings. Incidentally, a configuration similar to that in the first embodiment is designated by the same reference numeral, and the description is occasionally omitted. FIG. 13 is a perspective view that enlarges the scope-side connector and the processor-side connector; and FIG. 14 is a cross-sectional view that enlarges the scope-side connector and the processor-side connector.

In the endoscope system 1 according to the present embodiment, the removing section for removing the dirt is provided. Two heating sections (first heating section 114 and second heating section 116) are provided as the removing section.

The first heating section 114 is arranged in the periphery of the window 16A corresponding to the image signal reception section 64 in the side of the processor-side connector 12. When the shaft 22 is inserted into the hole 16, the first heating section 114 can heat the window 22A of the shaft 22 and the window 16A of the processor-side connector 12, and can remove mainly fogging among the dirt. The first heating section 114 can use any known heater as long as the heater can heat the window 22A and the window 16A, and the material, the structure and the like of the first heating section 114 are not limited.

The second heating section 116 is arranged in the periphery of the window 19 corresponding to the processor-side signal transception section 66 in the side of the processor-side connector 12. When the scope-side connector 18 and the processor-side connector 12 are connected to each other, the second heating section 116 can heat the window 23 of the scope-side connector 18 and the window 19 of the processor-side connector 12, and can remove mainly fogging among the dirt. The second heating section 116 can use any known heater as long as the heater can heat the window 23 and the window 19, and the material, the structure and the like of the second heating section 116 are not limited.

In the present embodiment, the two heating sections (first heating section 114 and second heating section 116) have been illustrated, but it is acceptable to have at least one heating section provided therein. In particular, the influence of the dirt is large between the image signal transmission section 42 and the image signal reception section 64. Accordingly, it is preferable to provide at least the first heating section 114.

Similarly to the first embodiment, the control section 76 can control the removing sections according to the three control flows illustrated in FIGS. 4 to 7 and FIG. 9. In addition, the operation of the removing section can be controlled by any combination of the three control flows.

What is claimed is:

1. An endoscope system which includes an endoscope having an image pickup section and a processor device for an endoscope, and optically communicates signals through a scope-side connector of the endoscope and a processor-side connector of the processor device for the endoscope, comprising:
    an optical communication section configured to optically communicate signals, wherein the optical communication section comprises a light source;
    a window that is arranged in an optical path of the optical communication section;
    a plurality of removing sections that remove dirt adhered on the window; and
    a controller configured to control an operation of the removing sections,
    wherein the controller controls the removing sections based on an input value of the optical communication section, and controls an output value based on the input value of the optical communication section.

2. The endoscope system according to claim 1, wherein each of the removing sections is an air blowing section that blows gas toward the window, and the air blowing section comprises a nozzle.

3. The endoscope system according to claim 2, wherein the processor device for the endoscope comprises a gas feeding section configured to feed a pressurized gas to the endoscope, and
    the gas is fed from the gas feeding section to the air blowing section,
    wherein the gas feeding section comprises a pump.

4. The endoscope system according to claim 1, wherein each of the removing sections is a wiper section configured to wipe the window, and the wiper section comprises a wiper blade.

5. The endoscope system according to claim 1, wherein each of the removing sections is a heating section configured to heat the window, and the heating section comprises a heater.

6. The endoscope system according to claim 1, wherein the controller detects whether or not the scope-side connector and the processor-side connector are connected to each other, and controls the removing sections.

7. The endoscope system according to claim 1, wherein
    the scope-side connector comprises a power receiving section that includes a power receiving coil configured to receive an electric power from the processor device for the endoscope in a wireless manner, and
    the processor-side connector comprises a power feeding section that includes a power feeding coil configured to feed the electric power to the endoscope in a wireless manner.

8. An endoscope system which includes an endoscope having an image pickup section and a processor device for an endoscope, and optically communicates an image signal and a control signal through a scope-side connector of the endoscope and a processor-side connector of the processor device for the endoscope, comprising:
    an image signal transmission section which is provided in the scope-side connector and is configured to transmit the image signal of the image pickup section as an optical signal;
    a scope-side signal transception section which is provided in the scope-side connector and is configured to optically communicate the control signal, wherein the scope-side signal transception section comprises a light source;
    an image signal reception section which is provided in the processor-side connector and is configured to receive the optical signal from the image signal transmission section of the endoscope;
    a processor-side signal transception section which is provided in the processor-side connector and is configured to optically communicate with the scope-side signal transception section, wherein the processor-side signal transception section comprises a light source;
    a plurality of removing sections that remove dirt adhered on a window for an image signal which is arranged in an optical path between the image signal transmission section and the image signal reception section, and/or a window for a control signal which is arranged in an optical path between the scope-side signal transception section and the processor-side signal transception section; and
    a controller that controls an operation of the removing sections,
    wherein the controller controls the removing sections based on an input value of an optical communication section, and controls an output value based on the input value of the optical communication section,
    wherein the optical communication section includes the image signal transmission section, the scope-side signal transception section, the image signal reception section and the processor-side signal transception section.

9. The endoscope system according to claim 8, wherein the scope-side connector comprises a power receiving section that includes a power receiving coil configured to receive an electric power from the processor device for the endoscope in a wireless manner, and the processor-side connector comprises a power feeding section that includes a power feeding coil configured to feed the electric power to the endoscope in a wireless manner.

* * * * *